United States Patent
Li et al.

(10) Patent No.: US 9,347,908 B2
(45) Date of Patent: May 24, 2016

(54) MOLECULAR IMPRINTED NANOSENSORS

(71) Applicants: Xiulan Li, Needham Heights, MA (US); Ranganathan Shashidhar, Needham Heights, MA (US); Yufeng Ma, Needham Heights, MA (US)

(72) Inventors: Xiulan Li, Needham Heights, MA (US); Ranganathan Shashidhar, Needham Heights, MA (US); Yufeng Ma, Needham Heights, MA (US)

(73) Assignee: Polestar Technologies, Inc., Needham Heights, MA (US)

( * ) Notice: Subject to any disclaimer, the term of this patent is extended or adjusted under 35 U.S.C. 154(b) by 481 days.

(21) Appl. No.: 13/668,804

(22) Filed: Nov. 5, 2012

(65) Prior Publication Data

US 2013/0092547 A1    Apr. 18, 2013

Related U.S. Application Data

(62) Division of application No. 12/510,414, filed on Jul. 28, 2009, now Pat. No. 8,313,633.

(51) Int. Cl.
| | |
|---|---|
| *G01N 27/06* | (2006.01) |
| *G01N 27/12* | (2006.01) |
| *B82Y 15/00* | (2011.01) |
| *G01N 27/327* | (2006.01) |
| *C25D 13/04* | (2006.01) |

(52) U.S. Cl.
CPC ............. *G01N 27/327* (2013.01); *C25D 13/04* (2013.01); *G01N 27/128* (2013.01)

(58) Field of Classification Search
CPC ......... B82Y 15/00; G01N 27/06; G01N 27/12
See application file for complete search history.

(56) References Cited

U.S. PATENT DOCUMENTS 6,807,842 B2 * 10/2004 Williams et al. ............... 73/23.2
7,384,589 B2    6/2008 Hart et al.
2006/0207878 A1    9/2006 Myung et al.

OTHER PUBLICATIONS

E. S. Forzani et al., Hybrid Amperometric and Conductometric Chemical Sensor Based on Conducting Polymer Nanojunctions, 79 Anal. Chem. 5217-5224 (2007).*
Jenkins, J. L. et al. Polymer-Based Lanthanide Luminescent Sensor for Detection of The Hydrolisis Product of The Nerve Agent Soman in Water. Anal. Chem. vol. 71, p. 373-378 (1999).
Holthoff, E. L. et al. Molecularly Templated Materials in Chemical Sensing. Analytica Chimica Acta vol. 594, p. 147-161 (2007).
Arnold, B.R. et al. Progress in the Development of Molecularly Imprinted Polymer Sensors. Johns Hopkins APL Technical Digest, vol. 20, No. 2 (1999).
Chen, F. et al. Electrochemical Approach for Fabricating Nanogap Electrodes with Well Controllable Separation, 86 Appl. Phys. Lett., 123105-123105-3 (2005).
Lin, Y-C. et al. Self-Aligned Nanolithography in a Nanogap, 9 Nano Lett., 2234-2238 (2009).
Cai. D. et al. A molecular-imprint nanosensor for ultrasensitive detection of proteins. Nature Nanotechnology Letters, vol. 5, Aug. 2010, pp. 597-601.
Kryscio, D.R. et al. Critical review and perspective of macromolecularly imprinted polymers. Acta Biomaterials 8 (2012), pp. 461-473.

* cited by examiner

*Primary Examiner* — Randy Boyer
(74) *Attorney, Agent, or Firm* — Burns & Levinson LLP; Orlando Lopez

(57) ABSTRACT

A molecular recognition sensor system is provided incorporating a molecular imprinted nanosensor device.

22 Claims, 5 Drawing Sheets

MOLECULAR IMPRINTED NANOSENSORS

CROSS REFERENCE TO RELATED APPLICATIONS

This application is a divisional of co-pending U.S. patent application Ser. No. 12/510,414, filed on Jul. 28, 2009 and entitled MOLECULAR IMPRINTED NANOSENSORS AND PROCESS FOR PRODUCING SAME, the entire contents of which are incorporated herein by reference herein in their entirety and for all purposes.

STATEMENT OF GOVERNMENT INTEREST

This invention was in part made with U.S. government support under contract No. W31P4Q-08-C-0401 awarded by DARPA. Accordingly, the government has certain rights in the invention.

BACKGROUND OF THE INVENTION

1. Field of the Invention

The present invention relates in general to a molecular recognition sensor system and process of making same which can be used for the detection of different chemicals in both the liquid and gaseous states and, more particularly, to a sensor device based on a molecular imprinted conducting polymer in nanoscale and process of making same.

2. Description of Related Art

Numerous methods and devices exist for the chemical detection of analytes. For example, prior art methods have attempted to detect analytes by imprinting analyte molecules into a polymer. These methods employ arranging polymerizable monomers around a template followed by polymerization and template removal. The result is a polymer having cavities of the same size and shape as the analyte. The transduction methods detecting the binding of the analytes into the cavities created in the polymer can be electrical, electrochemical, or optical etc, which measure the resistance/conductance, electrochemical properties and optical absorption of the imprinted polymer. See e.g. *Polymer-Based Lanthanide Luminescent Sensor For Detection Of The Hydrolisis Product Of The Nerve Agent Soman In Water*, Jenkens, et al., Anal. Chem. Vol 71, p. 373-378 (1999), *Molecularly Templated Materials in Chemical Sensing*, Ellen L. Holthoff, Frank V. Bright, Analytica Chimica Acta Vol 594, p. 147-161 (2007) and *Progress in the Development of Molecularly Imprinted Polymer Sensors*, Arnold, et al., Johns Hopkins APL Technical Digest, Vol. 20, No. 2 (1999) incorporated herein by reference.

U.S. Pat. No. 6,807,842 discloses a molecular recognition sensor system for detecting the presence and concentration of an analyte including a resistive sensor having a semi-conductive polymer film which swells when exposed to an analyte and interferents, together with a molecular imprinted resistive sensor having a semi-conductive polymer film imprinted with the analyte. The resistivity of the film is monitored during sensing to detect any changes in the resistivity of the film produced by the presence of an analyte.

In this system, the polymer film imprinted with an analyte swells when exposed to interferents. A circuit connected to the resistive sensor and the molecular imprinted resistive sensor detects a change in the resistance of the molecular imprinted resistive sensor when exposed to the analyte and interferents, and subtracts the change in the resistance of the molecular imprinted resistive sensor from the change in resistance of the resistive sensor to reduce the effect of any interferents on the change and resistance of the resistive sensor, thereby determining the presence and concentration of the analyte.

The resistivity of the semi-conductive polymer film is monitored during sensing. However, molecular imprinted polymer films often suffer long response time due to the limitation of diffusion. Also the sensitivity of the film sensor is limited because the lateral current shunting reduces the resistance change.

U.S. Pat. No. 7,384,589 discloses a nanoscale molecular imprinted polymer. However, the process of calming the polymer is complex, using a laser source for photoinitiation to produce nanoscale polymer features. The conventional imprinting process is time consuming and complicated by the use of cross-linkers. Further, the fabrication process restricts the detection methods to fluorescence and surface enhanced Raman spectroscopy, which increase the cost of the operation due to the integration of the optical components.

U.S. Patent Application Serial No. 20060207878 discloses conducting polymer nanowire sensors. One dimensional conducting polymer nanowires are defined with electron beam lithography and fabricated using electrochemical polymerization. The analyte-binding species and analyte are restricted to antibody-antigen, protein, polynucleotide and DNA. These sensors can be sensitive and selective. However, both the fabrication and the biological species for binding are expensive. Furthermore, biological binding restricts the future application.

Nevertheless, these molecular imprinted polymer devices suffer from the distinct disadvantage that they are designed to be specific to only one target analyte, are large, bulky, complex, delicate, and difficult to use.

It is therefore an object of this invention to provide a molecular recognition sensor system and method of using same.

It is another object of this invention to such a molecular recognition sensor system and method which can accurately detect an analyte.

It is a further object of this invention to provide such a molecular recognition sensor system and method which can accurately detect the concentration of an analyte.

It is another object of this invention to provide such a molecular recognition sensor system and method which can detect a plurality of analytes.

It is a further object of this invention to provide such a molecular recognition sensor system and method which can detect a plurality of analyte concentrations.

It is another object of this invention to provide such a molecular recognition sensor system and method which can detect a plurality of analyte in liquid and gaseous phases.

It is yet another object of this invention to provide such a molecular recognition sensor system which is compact, inexpensive, and easy to use.

It is a further object of this invention to provide such a molecular recognition sensor system which is simple in design and easily transportable.

BRIEF SUMMARY OF THE INVENTION

The present inventor, as a result of earnest research and development efforts, unexpectedly discovered a new and improved molecular recognition sensor system using a new and improved molecular recognition sensor and method of making same, which achieves the above-described objectives of the present invention.

In accordance with the present invention there is provided a molecular recognition sensor system incorporating a molecular imprinted nanosensor device formed by the process steps of:

(a) fabricating using photolithography a pair of metallic electrodes separated by a microscale gap onto a first electrical insulation layer formed on a substrate;

(b) applying a second electrical insulation layer on most of a top surface of said pairs of metallic electrodes;

(c) depositing additional metallic electrode material onto said electrode pairs using electrochemical deposition, thereby decreasing said microgap to a nano sized gap between said electrode pairs;

(d) electrochemically polymerizing in said nanogap conductive monomers containing a target analyte, thereby forming a molecular imprinted conducting polymer nanojunction in the gap between electrode pairs; and (e) immersing resultant sensor device in a solution and control the mechanical states of the polymer to remove the analyte molecules.

In a first preferred embodiment of the present invention, there is provided a molecular imprinted nanosensor device formed by the process steps of:

(a) applying a first electrical insulation layer on a surface of a silicon substrate;

(b) fabricating on said first electrical insulation layer using photolithography pairs of gold electrodes separated by a microscale gap;

(c) applying a second electrical insulation layer of silicon nitride on most of a top surface of said pairs of gold electrodes;

(d) depositing additional gold onto said gold electrodes using electrochemical deposition, thereby decreasing said microgap to a nano sized gap of from about 2 nm to 100 nm between said gold electrode pairs;

(e) electrochemically polymerizing in said nanogap conductive monomers containing a target analyte, thereby forming a conducting polymer nanojunction in the gap between gold electrode pairs.

In a second preferred embodiment of the present invention, there is provided in connection with the first preferred embodiment, a molecular imprinted nanosensor device formed by the further steps of immersing the sensor from step (e) in a solution which washes out the target analyte, and at the same time intermittently applying a voltage to the conducting polymer while it is immersed in said solution, thereby swelling and shrinking the conducting polymer to effect a more efficient extraction of target analyte from the conducting polymer.

In a third preferred embodiment of the present invention, there is provided in connection with the second preferred embodiment, a molecular imprinted nanosensor device formed by the further step of continuing application of an intermittent voltage to the conducting polymer until the current of the sensor stabilizes.

In a fourth preferred embodiment of the present invention, there is provided in connection with the first preferred embodiment, a molecular imprinted nanosensor device, wherein the electrochemical polymerization in step (e) is carried out in the presence of self-doped aniline, and sulfuric acid.

In a fifth preferred embodiment of the present invention, there is provided in connection with the fourth preferred embodiment, a molecular imprinted nanosensor device wherein the self-doped aniline is 3-aminobenzoic acid.

In a sixth preferred embodiment of the present invention, there is provided in connection with the fourth preferred embodiment, a molecular imprinted nanosensor device wherein the self-doped aniline is a derivative of aniline containing a carboxylic group or sulfonic acid group.

In a seventh preferred embodiment of the present invention, there is provided in connection with the fourth preferred embodiment, a molecular imprinted nanosensor device wherein in the electrochemical polymerization of step (e) the molar ratio between the regular aniline and the self-doped aniline is from about 3:1 to 1:1.

In an eighth preferred embodiment of the present invention, there is provided in connection with the fourth preferred embodiment, a molecular imprinted nanosensor device wherein in the electrochemical polymerization of step (e) the molar ratio between regular aniline and the self-doped aniline is about 1:1.

In a ninth preferred embodiment of the present invention, there is provided in connection with the fourth preferred embodiment, a molecular imprinted nanosensor device wherein in the electrochemical polymerization of step (e) the concentration of template analyte during the polymerization ranges from about 30 to 1000 ppm.

In a tenth preferred embodiment of the present invention, there is provided in connection with the fourth preferred embodiment, a molecular imprinted nanosensor device wherein in the electrochemical polymerization of step (e) the concentration of template analyte during the polymerization ranges from about 500 to 800 ppm.

In an eleventh preferred embodiment of the present invention, there is provided in connection with a fourth preferred embodiment, a molecular imprinted nanosensor device wherein in the electrochemical polymerization of step (e) the concentration of sulfuric acid in the polymerization is from about 0.05 to 2M.

In a twelfth preferred embodiment of the present invention, there is provided in connection with the fourth preferred embodiment, a molecular imprinted nanosensor device wherein in the electrochemical polymerization of step (e) the concentration of sulfuric acid in the polymerization is about 0.5M.

In a thirteenth preferred embodiment of the present invention, there is provided in connection with the first preferred embodiment, a molecular imprinted nanosensor device wherein the electrochemical deposition of gold in step (d) is continued until the microgap is reduced to a nanosized gap of about 30 nm.

In a fourteenth preferred embodiment of the present invention, there is provided in connection with the first preferred embodiment, a molecular imprinted nanosensor device wherein an open area of the second electrical insulation layer from about 4 to 400 $\mu m^2$.

In a fifteenth preferred embodiment of the present invention, there is provided in connection with the first provided embodiment a molecular imprinted nanosensor device wherein the polymerization in step (e) is carried out in either water, a mixture of water with ethanol, water with acetone or water with other solvents.

In a sixteenth preferred embodiment of the present invention, there is provided a process for the production of a molecular imprinted nanosensor device comprising the steps of:

(a) fabricating using photolithography a pair of metallic electrodes separated by a microscale gap onto a first electrical insulation layer formed on a substrate;

(b) applying a second electrical insulation layer on most of a top surface of said pairs of electrodes;

(c) depositing additional metallic electrode material onto said electrode pairs using electrochemical deposition, thereby decreasing said microgap to a nano sized gap between said electrode pairs;

(d) electrochemically polymerizing in said nanogap conductive monomers containing a target analyte, thereby forming a conducting polymer nanojunction in the gap between electrode pairs; and (e) immersing resultant sensor from step (d) in a solution which removes away target analyte, and intermittently applying a voltage to the conducting polymer while it is immersed in said solution, thereby swelling and shrinking conducting polymer to effect a more efficient extraction of target analyte from the conducting polymer.

In a seventeenth preferred embodiment of the present invention, there is provided an array of molecular imprinted nanosensor device produced by the first preferred embodiment, each nanosensor device being imprinted with a different analyte.

In an eighteenth preferred embodiment of the present invention, there is provided in connection with the first preferred embodiment, a molecular recognition sensor system comprising a molecular imprinted nanosensor device having its electrodes electrically connected to a voltage controller and a resistive sensor.

In a nineteenth preferred embodiment of the present invention, there is provided a molecular imprinted nanosensor device formed by the process steps of:

(a) applying a first electrical insulation layer on a surface of a substrate selected from the group consisting of silicon, glass, quartz, sapphire, plastic, ceramic, metal, and flexible materials;

(b) fabricating on said first electrical insulation layer using photolithography pairs of electrodes formed from a metal selected from the group consisting of platinum, palladium, copper and gold, said resultant electrodes being separated by a microscale sized gap;

(c) applying a second electrical insulation layer of a material selected from the group consisting of silicon nitride, silicon dioxide, and other electrical insulating materials on most of a top surface of said pairs of electrodes;

(d) depositing additional electrode materials onto said electrical pairs using electrochemical deposition, thereby decreasing said microgap to a nanosized gap of from about 2 to 100 nm between said electrode pairs; and (e) electrochemically polymerizing in said nanogap a conducting polymer selected from the group consisting of polyaniline, polypyrrole, polythiophene, polyphenylene, polyacetylene, and derivatives thereof in the presence of a target analyte together with a self-doped monomer selected from the group consisting of 3-aminobenzoic acid and other derivatives thereof which contain a carboxylic group or sulfonic group.

In a twentieth preferred embodiment of the present invention, there is provided in connection with the nineteenth preferred embodiment, a molecular imprinted nanosensor device formed by the further steps of immersing the sensor from step (e) in a solution which removes away target analytes, intermittently applying a voltage to the conductive polymer while it is immersed in said solution, thereby swelling and shrinking the conducting polymer to effect a more efficient extraction of target analyte from the conducting polymer.

DETAILED DESCRIPTION OF THE INVENTION

Figure 1:
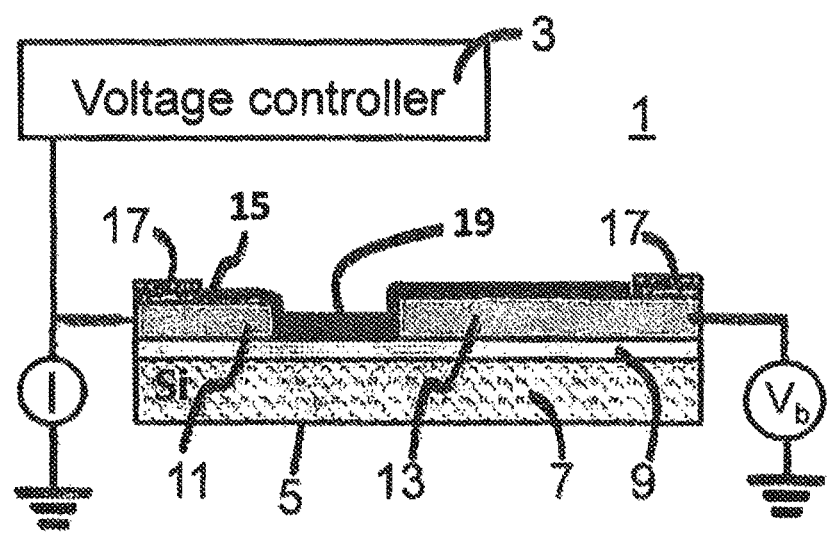
FIG. 1 is a cross-sectional view of a molecular recognition sensor system of the present invention, illustrating the configuration of the components of the molecular imprinted nanosensor device employed in the system.

A molecular recognition sensor system fabricated according to the present invention is shown generally at 1 in FIG. 1, and comprises voltage controller and associated circuitry shown generally at 3, and a molecular imprinted nanosensor device shown generally at 5. In a preferred embodiment, the molecular imprinted nanosensor 5 is based on a silicon substrate 7. In another preferred embodiment, the molecular imprinted nanosensor device 5 is based on a substrate material selected from the group consisting of silicon, glass, quartz, sapphire, plastic, ceramic, metal, other semiconductive materials, or a flexible material. A first electrical insulation layer 9 is formed on one surface of substrate 7. The first electrical insulation layer can be formed of a material preferably selected from the group consisting of silicon oxide, silicon nitride, hafnium silicate, zirconium silicate, hafnium dioxide, zirconium dioxide, aluminum oxide etc.

Pairs of electrodes 11, 13 are then defined on the first electrical insulation layer 9 using photolithography and fabricated using conventional Si processing methods. Electrodes 11, 13 are preferably formed of platinum, palladium, copper or other metal, more preferably from gold. Electrode pairs 11, 13 are initially separated by a micro size gap (not shown) during their formation using photolithography.

Most upper surfaces 15 of electrodes 11, 13 are then covered with a second insulation layer 17. The insulation layer 17 is preferably formed of silicon dioxide or other insulation materials, more preferably by silicon nitride.

The initial micro size gap between electrodes 11, 13 is then reduced or decreased in size by electrochemical deposition of additional electrode materials onto the surface of the electrodes in the micro size gap. In a preferred embodiment, electrode pairs 11, 13 are formed of gold, and preferably platinum, palladium, copper or other metal, more preferably gold is then used in the electrochemical deposition process to further decrease the microgap.

In a preferred embodiment, the electrochemical deposition of electrode material is carried out until the micro size gap is reduced to a nano size gap of from about 2 to 100 nm, more preferably about 30 nm. The size of the nanojunction can be controlled by adjusting the voltage, current and deposition time in the electrochemical deposition process.

Sensors in nanoscale such as in the present invention have several advantages, such as good conductivity, fast response, and high sensitivity. This electrochemical deposition process can be carried out simultaneously on different electrode pairs formed on a substrate 7. The fabrication of nano sized gaps produced in this manner is more efficient and less expensive than conventional electron beam lithography.

A polymer nanojunction shown generally at 19 is then fabricated to bridge the resultant nanogap between electrodes 11, 13. This is accomplished by electrochemically polymerizing conductive monomers containing a target analyte in the gap between electrodes 11, 13 to form a conducting polymer 19 in this nanojunction. The conducting polymer 19 is preferably selected from the group consisting of polypyrrole, polythiophene, polyphenylene, polyacetylene and derivatives thereof. More preferably, conducting polymer 19 is formed from a polyaniline copolymer containing target analyte molecules.

In a preferred embodiment, the monomer used to form the electrically conductive polymer nanojunction 19 also contains a self-doped aniline to retain the conductivity of the conducting polymer over a wide pH range. In a preferred embodiment, the self doped aniline is 3-aminobenzoic acid or other derivatives thereof which contain either a carboxylic group or sulfonic group. Preferably, sulfuric acid is used in the polymerization to dope aniline, but other acids can also be used such as hydrochloric acid, chloric acid, perchloric acid, nitric acid, and the like In the polymerization and molecular imprinting steps, the molar ratio between regular aniline and self-doped aniline is preferably from about 3:1-1:1, depending upon the pH value of the detection environment. More preferably, the molar ratio between regular aniline and self-doped aniline is about 1:1. The polymerization of electrochemical imprinted polymer 19 is preferably carried out in water, but it can also be carried out in a mixture of water with ethanol, water with acetone, or water with other solvents.

The concentration of the target analyte in the polymerization is preferably from about 30 to 1000 ppm, more preferably from about 500 to 800 ppm. The concentration of sulfuric acid in the polymerization is preferably from about 0.05 to 2M, more preferably about 0.5M. Since molecular printing creates cavities exactly the same as the analyte molecules in size and shape, the resultant sensors are highly selective.

The resultant size of conducting polymer nanojunction is preferably from about 2 to 100 nm, more preferably about 30 nm. The size of the nanojunction is determined by the size of the nanogap which can be controlled by the deposition time and current used in depositing additional electrode material onto electrode pairs 11, 13.

The resultant conducting polymer 19 is used in the present invention as the backbone of the nanosensor device 5. The conducting polymer 19, such as polyaniline, is electronic conductive, and is easy to process by electrochemical polymerization. Compared to conventional molecular imprinted polymer processes, target analytes can be incorporated into the conducting polymer in a single-step process during polymerization.

Figure 2:
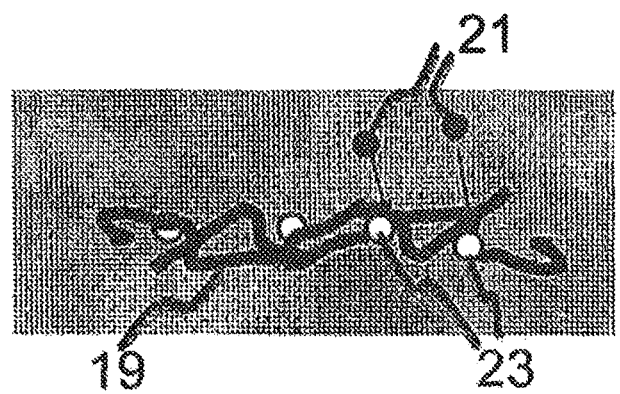
FIG. 2 is a schematic representation of a polymer in a molecular imprinted nanosensor device of the present invention, illustrating in particular the conducting polymer, analyte molecules, and recognition sites.

After formation of polymer nanojunction 19, target analyte molecules 21 are extracted from the conducting polymer 19, leaving binding sites 23 complimentary in size and shape (see FIG. 2).

In conventional molecular imprinting, washing or soaking the sensor in solvent is used to wash away the imprinted target analyte molecules. However, in the present invention, after the sensor is immersed in a analyte molecule free solvent liquid, the electrode potential is cycled. During the cycling, conducting polymer 19 swells and shrinks back to the original state. The swelling during cycling effects more efficient extraction of target analyte 21 molecules from the conducting polymer backbone which offers high sensitivity of the sensor device 5. The extraction step ends when the current of the sensor stabilizes.

In a preferred embodiment, molecular imprinted nanosensors 5 as described above can be fabricated in array for real time simultaneous detection of different analytes. In such cases, different target analytes are used in the conducting polymers 19 between electrode pairs 11, 13.

In a preferred embodiment, the open area of the nanojunction exposed to liquid or gas is from about 4 to 400 $\mu m^2$ and the ionic leakage current ranges from about 1 pA to 1 nA. The smaller the ionic leakage current, the more sensitive is the sensor. Since the ionic current is very small, the current of the nanosensor, is tens of nanoamperes to tens of microamperes. The preferred current range is hundreds of nanoamperes. In a preferred embodiment, the open area of the second layer insulation area is 100 $\mu m^2$.

Figure 3:
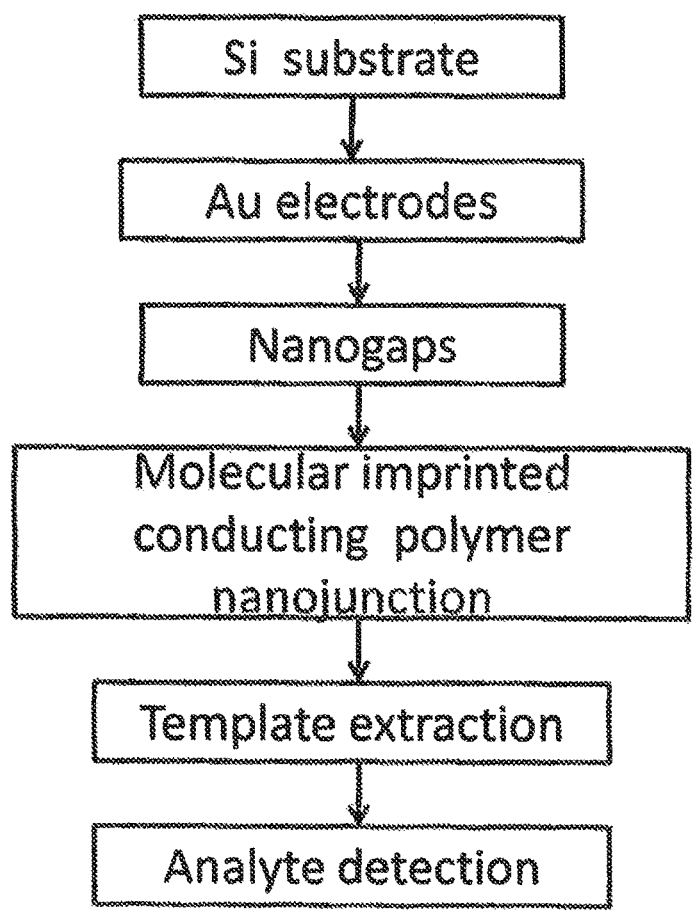
FIG. 3 is a flow chart of process steps used in forming the molecular imprinted nanosensor device of the present invention, illustrating the sequence of steps required in the process of forming the molecular imprinted nanosensor.

A flow chart shown in FIG. 3 illustrates the above-described sequence of steps which are employed in forming the molecular imprinted nanosensors 5 of the present invention. Flow chart, FIG. 3, illustrates a preferred embodiment of the present invention in which silicon is used as substrate 7.

Gold is used in forming electrodes 11, 13. The molecular imprinted conducting polymer 19 is preferably formed from polyaniline and self-doped aniline (3-aminobenzoic), and analyte 21 extraction is preferably employed using electrode potential cycling to facilitate removal of target analyte molecules 21 and formation of recognition binding sites 23.

After formation of the binding sites, the interaction of target analytes and the molecular imprinted nanosensor 5 is transduced (converted) into an electrical signal. The molecular imprinted nanosensor shown generally at 1 is robust and can be reused. For the detection of a target analyte in the liquid phase, the conductance of conducting polymer nanojunction is controlled at the most sensitive state with a voltage controller 3 which offers high sensitivity. For the detection of a target analyte in the gaseous phase, voltage control is not needed. The detection both in liquid and gas phases occurs in real time. Molecular imprinted nanosensors 5 can be used for continuously monitoring target analytes.

By imprinting different target analytes into different conducting polymer nanojunctions, molecular imprinted nanosensor devices are capable of simultaneous detection of multiple target analytes at the same time.

Molecular imprinted nanosensor 5 is capable of detection of a wide range of target analytes. They can be organophosphate chemical nerve agents such as sarin and somin; volatile organic compounds such as xylene, toluene; pesticides such as DDT (Dichloro-diphenyl-Trichloroethane), dinitro-o-cresol; persistent organic pollutants, such as hexachlorobenzene, herbicides such as atrazine; drugs such as prulifloxacin, morphine; and explosives such as TNT (trinitrotoluene), and HMX (cyclotetramethylenetetranitramine).

The cost of fabrication of nanoscaled gaps and nanosensors according to the present invention is relatively small. Electrochemical deposition is used to shrink the microscaled gap to nanoscale, and electrochemical polymerization is used to fabricate the nanosensor 5. Both of these processes are capable of being used in mass production of the nanosensors of the present invention. Nanosensors produced according to the present invention exhibit a response of molecular imprinted nanosensor device to analytes on a linear basis from 0 to 1 ppm (1000 ppb), which facilitates ease of calibration.

The following examples set forth a preferred process of producing a molecular imprinted nanosensor of the present invention. However, this example is not intended to limit in any way the scope and breadth of the present invention.

EXAMPLE 1

Volatile organic compound o-xylene was imprinted and detected with molecular imprinted nanosensor. A gold nanogap was first achieved by electrochemically depositing gold materials onto the gold pair of electrodes separated by a 1 μm gap. This nanogap was then bridged with polyaniline copolymer by cycling electrode potential in a solution containing 24 mM regular aniline, 24 mM self-doped aniline (3-aminobenzoic acid), 0.5M sulfuric acid as supporting electrolyte and 800 ppm o-xylene as the target analyte molecule. After formation of the molecular imprinted nanosensor, the analyte molecules were then extracted by cycling the electrode in an analyte free sulfuric acid (0.1M) and detection solution. During the cycling, the solution was replaced for 3-6 times until the current of the nanosensor was stabilized.

Figure 4:
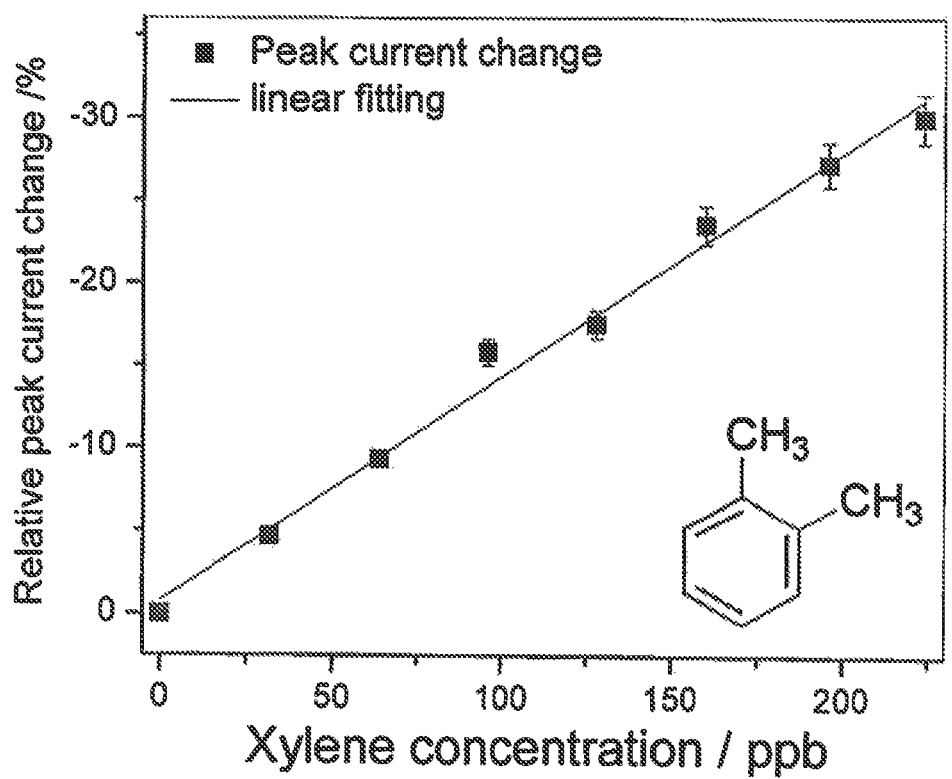
FIG. 4 is a graph of relative peak current change versus xylene concentration, illustrating the advantages of employing the molecular imprinted nanosensor of the present invention.

O-xylene was then detected in pH 6.5 solution. Upon exposure to 32 ppb on xylene, a distinct decrease occurred in the peak current of the sensor. With the concentration range from 0 to 250 ppb, the response of the electric molecular imprinted nanosensor to o-xylene was found to be linear as shown in the graph in FIG. 4.

EXAMPLE 2

Figure 5:
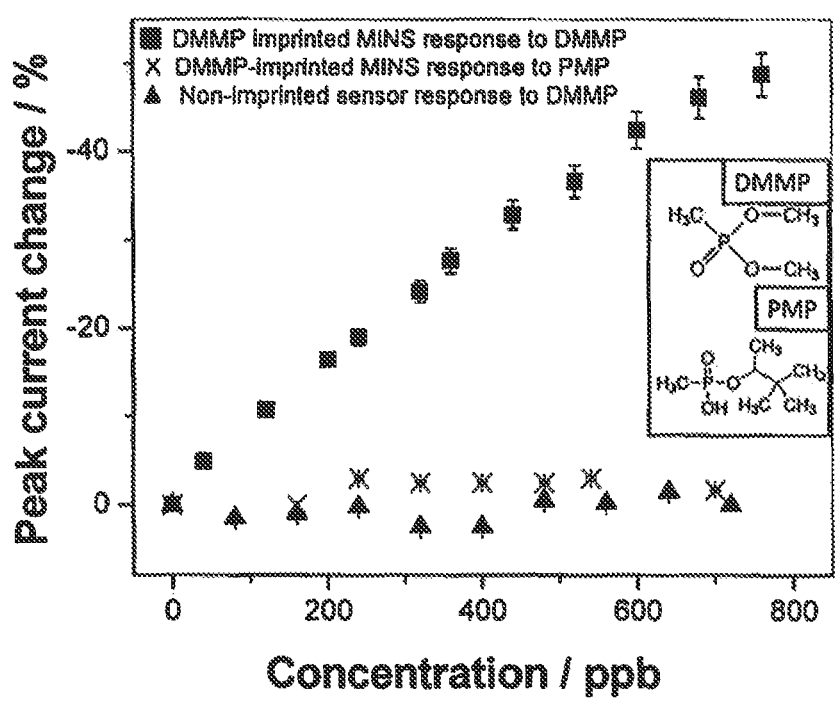
FIG. 5 is a graph of relative peak current change of DMMP and non-imprinted nanosensors versus the concentration of DMMP and PMP, illustrating the high sensitivity and great selectivity of the molecular imprinted nanosensor of the present invention.

Detection of a chemical nerve agent simulant, DMMP (Dimethyl methylphosphonate) was demonstrated with DMMP-imprinted nanosensor (solid squares in FIG. 5). The experimental conditions are the same as in EXAMPLE 1, except the template molecules are DMMP in this case. In order to prove that molecular imprinted nanosensor does provide specific binding sites of the analytes, the response of non-imprinted nanosensor to DMMP is also shown in FIG. 5 (solid triangulars). Compared to DMMP-imprinted nanosensor, non-imprinted nanosensor has almost no response to DMMP. Further, DMMP-imprinted nanosensor is sensitive to DMMP, but has no response to PMP (Pinacolyl methyl phosphonate), even the two molecules are very similar on molecular structures, which indicates the great selectivity of our molecular imprinted nanosensor. This work demonstrated that molecular imprinted nanosensor is capable for the detection of toxic organic phosphate chemical nerve agents.

LIST OF DRAWING ELEMENTS

1: molecular recognition sensor system
3: voltage controller and associated circuitry
5: molecular imprinted nanosensor device
7: substrate
9: first electrical insulation layer
11: electrode
13: electrode
15: upper surfaces of electrodes 11, 13
17: insulation layer
19: conducting polymer
21: analyte
23: recognition binging sites

What is claimed is:
1. A molecular imprinted nanosensor device formed by the process steps of:
 (a) applying a first electrical insulation layer on a surface of silicon substrate;
 (b) fabricating on said first electrical insulation layer using photolithography pairs of gold electrodes separated by a microscale gap;
 (c) applying a second electrical insulation layer of silicon nitride onto most of a top surface of said pairs of gold electrodes;
 (d) depositing additional gold onto said gold electrodes using electrochemical deposition, thereby decreasing said microgap to a nanosized gap of from about 2 to 100 nm between said gold electrode pairs;
 (e) electrochemically polymerizing in said nanogap aniline monomers in the presence of a target analyte; and
 (f) extracting target analyte molecules from polymerized aniline monomers,
 thereby forming a molecularly imprinted conducting polymer nanojunction in the gap between gold electrode pairs.

2. The molecular imprinted nanosensor of claim 1, wherein extracting the target analyte molecules comprises:
 (a) immersing the sensor from step (e) in a solution which removes away the target analyte, and
 (b) intermittently applying a voltage to the conducting polymer while it is immersed in said solution,
 (c) thereby swelling and shrinking the conducting polymer to effect a more efficient extraction of target analyte from conducting polymer.

3. The molecular imprinted nanosensor device of claim 2, comprising the further step of continuing application of an intermittent voltage to the conducting polymer until the current of the sensor stabilizes.

4. The molecular imprinted nanosensor device of claim 1, wherein the electrochemical polymerization in step (e) is carried out in the presence of self-doped aniline, and sulfuric acid.

5. The molecular imprinted nanosensor device of claim 4, wherein the self-doped aniline is 3-aminobenzoic acid.

6. The molecular imprinted nanosensor device of claim 4, wherein the self-doped aniline is a derivative of aniline containing a carboxylic group or sulfonic acid group.

7. The molecular imprinted nanosensor device of claim 4, wherein in the electrochemical polymerization in step (e), the molar ratio between the regular aniline and the self-doped aniline is from about 3:1 to 1:1.

8. The molecular imprinted nanosensor device of claim 4, wherein in the electrochemical polymerization in step (e), the molar ratio between the regular aniline and the self-doped aniline is about 1:1.

9. The molecular imprinted nanosensor device of claim 4, wherein in the electrochemical polymerization in step (e), the concentration of analyte during the polymerization ranges from about 30 to 1000 ppm.

10. The molecular imprinted nanosensor device of claim 4, wherein in the electrochemical polymerization in step (e), the concentration of analyte during the polymerization ranges from about 500 ppm to 800 ppm.

11. The molecular imprinted nanosensor device of claim 4, wherein in the electrochemical polymerization in step (e), the concentration of sulfuric acid in the polymerization is from 0.05M to 2M.

12. The molecular imprinted nanosensor device of claim 4, wherein in the electrochemical polymerization in step (e), the concentration of sulfuric acid in the polymerization is about 0.5M.

13. The molecular imprinted nanosensor device of claim 1, wherein the electrochemical deposition of gold in step (d) continues until the microgap is reduced to a nanosized gap of about 30 nm.

14. The molecular imprinted nanosensor device of claim 1, wherein an open area of the second electrical insulation layer is from about 4 to 400 µm².

15. The molecular imprinted nanosensor device of claim 1, wherein the polymerization in step (e) is carried out either in water, a mixture of water with ethanol, water with acetone, or water with other solvents.

16. An array of molecular imprinted nanosensors devices produced by the process of claim 1, each imprinted with a different analyte.

17. A molecular recognition sensor system comprising a molecular imprinted nanosensor device of claim 1, having its electrodes electrically connected to a voltage controller and a resistive sensor.

18. A molecular imprinted nanosensor device formed by the process steps of:
(a) applying a first electrical insulation layer on a surface of a substrate selected from the group consisting of silicon, glass, quartz, sapphire, plastic, ceramic, metal, and a flexible material;
(b) fabricating on said first electrical insulation layer using photolithography pairs of electrodes formed from a metal selected from the group consisting of platinum, palladium, copper, and gold, said electrodes being separated by a microscale gap;
(c) applying a second electrical insulation layer of a material selected from the group consisting of silicon nitride, silicon dioxide, and other insulating materials on most of a top surface of said pairs of electrodes;
(d) depositing additional electrode materials selected from the group consisting of gold, platinum, palladium, copper using electrochemical deposition, thereby decreasing said microgap to a nanosized gap of from about 2 to 100 nm between said electrode pairs;
(e) electrochemically polymerizing in said nanogap a conducting polymer selected from the group consisting of polyaniline, polypyrrole, polythiophene, polyphenylene, polyacetylene, and derivatives thereof, in the presence of a target analyte together with a self-doped monomer selected from the group consisting of 3-aminobenzoic acid and other derivatives thereof which contain a carboxylic group or sulfonic group; and
(f) extracting target analyte molecules from polymerized conducting polymer,
thereby forming a molecularly imprinted polymerized conducting polymer nanojunction in the nanosized gap between said electrodes.

19. The molecular imprinted nanosensor device of claim 18, wherein extracting the target analyte molecules comprises:
(a) immersing the sensor from step (e) of claim 18 in a solution which removes away target analytes, and
(b) intermittently applying a voltage to the conductive polymer while it is immersed in said solution,
(c) thereby swelling and shrinking the conducting polymer to effect a more efficient extraction of target analyte from the conducting polymer.

20. A molecularly imprinted nanosensor device comprising:
at least one pair of electrodes disposed on an insulation layer, one electrode from the at least one pair of electrodes separated from another electrode from the at least one pair of electrodes by a nanosized gap of about 2 to 100 nm; and
a molecularly imprinted conducting polymer bridging the nanosized gap between said one electrode and said another electrode, the molecularly imprinted conducting polymer being imprinted for an analyte;
wherein the molecularly imprinted nanosensor sensor having only the molecular imprinted conducting polymer disposed between said one electrode and said another electrode is sufficient to measure the concentration of the analyte.

21. The molecular imprinted nanosensor device of claim 20 wherein material of said at least one pair of electrodes is selected from the group consisting of platinum, palladium, copper, and gold.

22. The molecular imprinted nanosensor device of claim 20 wherein the insulation layer is disposed on a substrate.

* * * * *